US00PP30034P2

(12) United States Plant Patent
Wright

(10) Patent No.: US PP30,034 P2
(45) Date of Patent: Dec. 25, 2018

(54) ***ALOE* PLANT NAMED 'OVROCKS03'**

(50) Latin Name: ***Aloe* hybrid**
Varietal Denomination: OVROCKS03

(71) Applicant: Ovata B.V., Bleiswijk (NL)

(72) Inventor: Dick Wright, Fallbrook, CA (US)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/932,022

(22) Filed: Jan. 25, 2018

(30) Foreign Application Priority Data

Oct. 12, 2017 (QZ) ..... PBR 2017/2563

(51) Int. Cl.
*A01H 5/00* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct variety of *Aloe* plant named 'OVROCKS03' which is characterized by a globular plant form with foliage arranged in a compact basal rosette, deltoid to narrowly deltoid succulent foliage which densely covered with prominent raised protuberances appearing as ribs and soft spines, and the stability of these characteristics from generation to generation.

4 Drawing Sheets

Latin name of the genus and species: The Latin name of the genus and species of the novel variety disclosed herein is *Aloe* hybrid.

Variety denomination: The inventive variety of *Aloe* disclosed herein has been given the variety denomination 'OVROCKS03'.

CROSS REFERENCE TO RELATED APPLICATIONS

This application claims priority to the Community Plant Variety Rights application number 2017/2563, filed on Oct. 12, 2017, which is herein incorporated by reference.

BACKGROUND OF THE INVENTION

Parentage: 'OVROCKS03' is a seedling selection resulting from the controlled pollination of an unnamed *Aloe haworthioides* plant (unpatented), the seed parent, with an unnamed *Aloe descoingsii* plant (unpatented), the pollen parent. The crossing was made by the inventor in January of 2009 at a greenhouse in Fallbrook, Calif. In March of 2010, one seedling was observed which exhibited an abundance of protuberances presenting as raised ribs and soft spines when compared to the parent plants and all other progeny. After confirming the stability of the unique characteristics first observed, the new plant was selected for commercialization and given the name, 'OVROCKS03'.

Asexual Reproduction: Asexual reproduction of the new cultivar 'OVROCKS03', by way of rooting leaf cuttings, was first initiated in March of 2010 at a commercial greenhouse in Bleiswijk, the Netherlands. The claimed plant has since been asexually propagated by way of meristematic tissue culture propagation. Through eight subsequent generations, the unique features of this cultivar have proven to be stable and true to type.

SUMMARY OF THE INVENTION

The cultivar 'OVROCKS03' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS03'. These characteristics in combination distinguish 'OVROCKS03' as a new and distinct *Aloe* cultivar:

1. 'OVROCKS03' exhibits a globular plant form with foliage arranged in a compact basal rosette; and
2. 'OVROCKS03' exhibits deltoid to narrowly deltoid succulent foliage which is held upright; and
3. 'OVROCKS03' exhibits foliage which densely covered with prominent raised protuberances appearing as ribs and soft spines.

BOTANICAL DESCRIPTION OF THE PLANT

Figure 1:
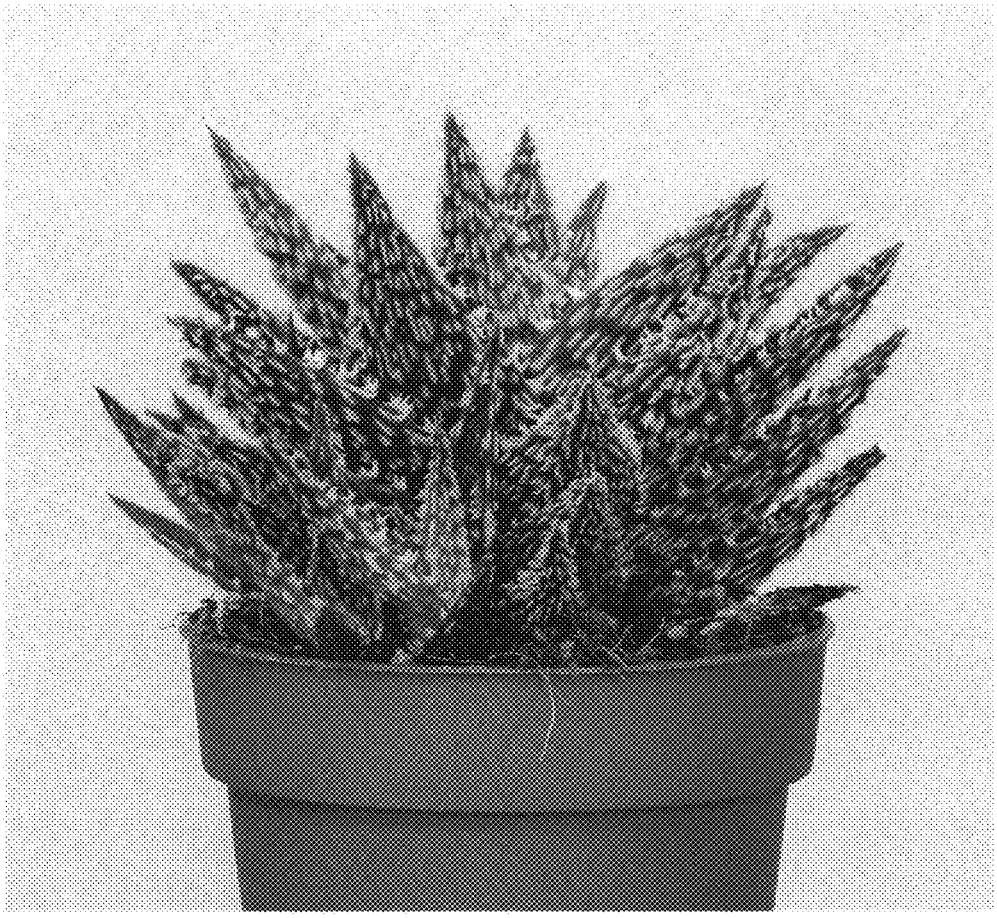
FIG. 1 illustrates, as nearly true as it is reasonably possible to make the same in color photographs of this type, an exemplary plant of 'OVROCKS03' grown in a commercial greenhouse in Bleiswijk, the Netherlands. This plant is approximately 12 months old, shown planted in an 8.5 cm container.
Figure 2:
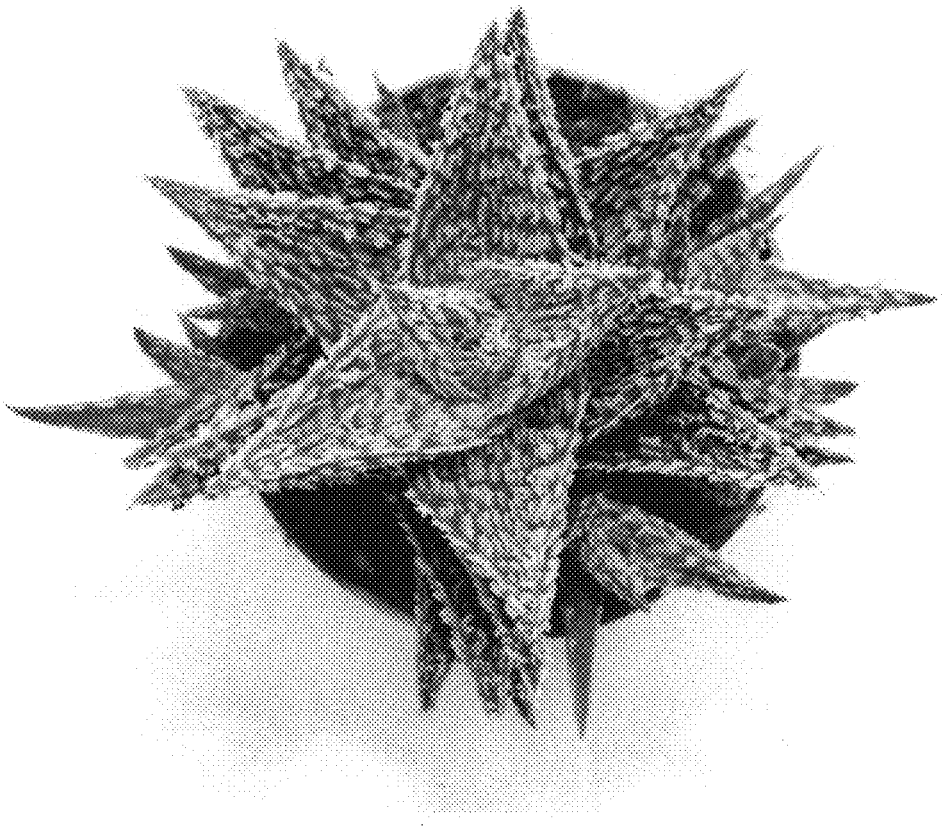
FIG. 2 illustrates, as nearly true as it is reasonably possible to make the same in color photographs of this type, the typical foliage arrangement of 'OVROCKS03'.
Figure 3:
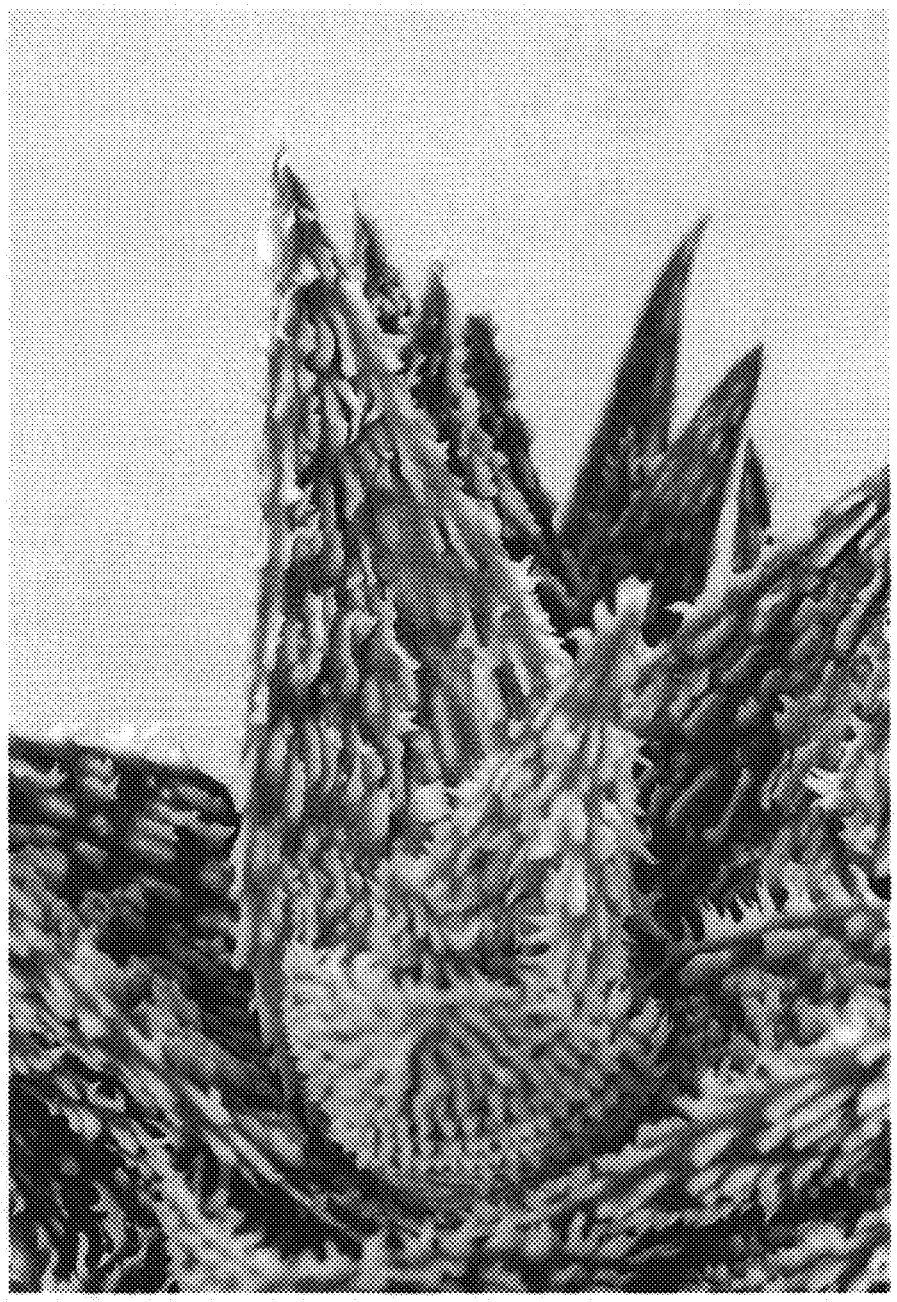
FIG. 3 illustrates, as nearly true as it is reasonably possible to make the same in color photographs of this type, the adaxial surface of the mature foliage 'OVROCKS03'.
Figure 4:
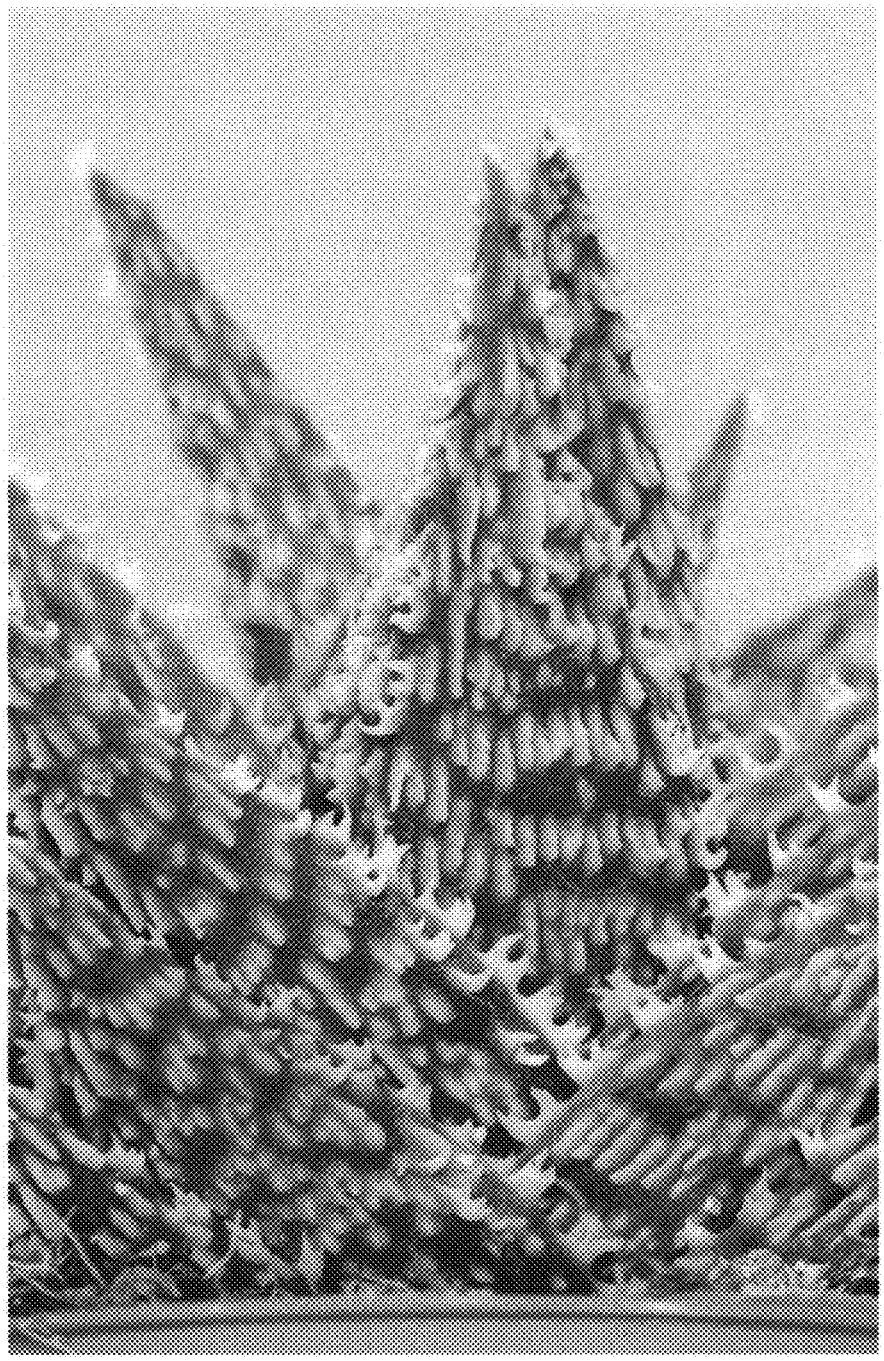
FIG. 4 illustrates, as nearly true as it is reasonably possible to make the same in color photographs of this type, the abaxial surface of the mature foliage 'OVROCKS03'.

The following observations and measurements made in June of 2017 describe averages from a sample set of six specimens of 12 months old 'OVROCKS03' plants grown in 8.5 cm nursery containers at a commercial greenhouse in Bleiswijk, the Netherlands. Plants were produced using conventional greenhouse production protocols for *Aloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS03' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS03' and comparisons with the parents and closest known comparator are provided below.

Plant description:

*Growth habit*.—Succulent perennial with foliage growing in a non-branched basal rosette.

*Plant form*.—Globular.

*Height from soil level to top of foliar plane*.—7.5 cm.

*Plant spread*.—Average of 11.8 cm.

*Growth rate*.—Low.

*Plant vigor*.—Moderate.

*Propagation*.—Type — Leaf cuttings. Time to initiate rooting — Approximately 2 months at 22 degrees Celsius. Crop time — Approximately 12 months to produce a marketable plant in an 8.5 cm container.

*Disease and pest resistance or susceptibility*.—Neither resistance nor susceptibility to typical *Aloe* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Spirally placed in a rosette.

*Division*.—Simple.

*Attachment*.—Sessile.

*Quantity*.—Approximately 25 leaves per rosette.

*Shape*.—Deltoid to narrow deltoid succulent leaves.

*Dimensions*.—5.8 cm long, 2.6 cm wide, and 0.5 cm thick, on average.

*Aspect*.—Flat.

*Attitude*.—At an average angle of 45 degrees to the soil level.

*Apex*.—Acuminate with a soft mucronate tip.

*Base*.—Broad cuneate.

*Margin*.—Densely dentate; teeth have an average length of 0.1 cm and are colored green-white, nearest to RHS 157D but lighter. Margins are not undulated or lobed.

*Texture, adaxial surface*.—Glabrous and densely covered with raised protuberances, presenting as small ribs and small soft spines; on average, ribs are 0.2 cm long, 0.05 cm wide, and 0.075 cm high; spines are 0.1 cm in diameter and 0.1 cm high, on average.

*Texture, abaxial surface*.—Glabrous and densely covered with protuberances, presenting as small ribs and small soft spines; on average, ribs are 0.2 cm long, 0.05 cm wide, and 0.075 cm high; spines are 0.1 cm in diameter and 0.1 cm high, on average.

*Luster, adaxial surface*.—Matte.

*Luster, abaxial surface*.—Matte.

*Color*.—Juvenile foliage, adaxial surface — Green, nearest to RHS 137C, and fading to yellow-green towards the base, nearest to RHS 144C; protuberances are colored green-white, nearest to RHS 157B but lighter. Juvenile foliage, abaxial surface — Green, nearest to RHS 137C, and fading to yellow-green towards the base, nearest to RHS 144C; protuberances are colored green-white, nearest to RHS 157B but lighter. Mature foliage, adaxial surface — Nearest to in between green, RHS NN137A, and yellow-green, RHS 147A; leaf densely covered with ribs and spines which are colored green-white, nearest to RHS 157B but lighter. Mature foliage, abaxial surface — Nearest to in between green, RHS NN137A, and yellow-green, RHS 147A; leaf densely covered with ribs and spines which are colored green-white, nearest to RHS 157B but lighter. Venation — No venation is visible.

*Petiole*.—No petiole; leaves are sessile.

Inflorescence: No flowering has been observed to date.

COMPARISONS WITH THE PARENT PLANT

Plants of the new cultivar 'OVROCKS03' differ from the seed parent, an unnamed *Aloe haworthioides* plant (not patented), in the following characteristics described in Table 1 below.

COMPARISON WITH SEED PARENT

TABLE 1

| Characteristic | 'OVROCKS03' | The seed parent. |
|---|---|---|
| Abundance of foliage. | Fewer leaves than the seed parent. | More leaves than 'OVROCKS03'. |
| Foliage shape. | Deltoid to narrow deltoid. | Narrowly deltoid. |
| Size of the spined protuberances. | Shorter spines. | Longer spines. |
| General coloration of the protuberances. | Green-white. | White. |

Plants of the new cultivar 'OVROCKS03' differ from the pollen parent, an unnamed *Aloe descoingsii* plant (not patented), in the following characteristics described in Table 2 below.

COMPARISON WITH POLLEN PARENT

TABLE 2

| Characteristic | 'OVROCKS03' | The pollen parent. |
|---|---|---|
| Foliage attitude. | More upright than the 'OVROCKS031. | Less upright than pollen parent. |
| Abundance of protuberances on the foliage. | Very abundant. | None present. |
| Foliage size. | Smaller than the pollen parent. | Larger than 'OVROCKS03'. |
| General coloration of entire rosette. | Lighter green. | Darker green. |

COMPARISONS WITH THE CLOSEST KNOWN COMPARATOR

Plants of the new cultivar 'OVROCKS03' differ from the commercial variety, *Aloe rauhii* 'DEMI' (U.S. Plant Pat. No. 29,485) in the following characteristics described in Table 3 below.

COMPARISON WITH COMPARISON PLANT

TABLE 3

| Characteristic | 'OVROCKS03' | 'DEMI' |
|---|---|---|
| Growth habit. | More compact. | Less compact. |
| Foliage shape. | Deltoid to narrow deltoid. | Broad ovate to near deltoid. |
| Protuberances on the foliage. | An abundance of protuberances, presenting as small ribs and soft spines. Arrangement appears less organized than the protuberances | An abundance of narrow, elongated protuberances which are tightly arranged into numerous longitudinal rows across the entire leaf. of 'DEMI'. |
| Length of protuberances. | Longer than those of 'DEMI'; more raised off of the leaf surface, | Shorter than those of 'OVROCKS03'; less raised off of the leaf surface. |

That which is claimed is:

1. A new and distinct variety of *Aloe* plant named 'OVROCKS03', substantially as described and illustrated herein.

* * * * *